United States Patent [19]

Pennington

[11] Patent Number: 4,882,443

[45] Date of Patent: * Nov. 21, 1989

[54] ALKYLENE OXIDES PRODUCTION FROM C7 TO C22 OLEFINS USING MOLTEN NITRATE SALT CATALYST

[75] Inventor: B. Timothy Pennington, Sulphur, La.

[73] Assignee: Olin Corporation, Cheshire, Conn.

[*] Notice: The portion of the term of this patent subsequent to Nov. 15, 2005 has been disclaimed.

[21] Appl. No.: 238,654

[22] Filed: Aug. 31, 1988

Related U.S. Application Data

[63] Continuation-in-part of Ser. No. 929,552, Nov. 12, 1986, Pat. No. 4,785,123.

[51] Int. Cl.$^4$ ............................................. C07D 301/06
[52] U.S. Cl. ..................................... 549/532; 549/533
[58] Field of Search ......................... 549/533, 531, 523

[56] References Cited

U.S. PATENT DOCUMENTS

| | | | |
|---|---|---|---|
| 2,366,724 | 1/1945 | Gardner | 549/523 |
| 2,530,509 | 11/1950 | Cook | 549/523 |
| 3,132,156 | 5/1964 | Lemon et al. | 549/523 |
| 3,641,157 | 2/1972 | Riegel et al. | 549/523 |
| 3,647,358 | 3/1972 | Greenberg | 23/2 R |
| 3,786,109 | 1/1974 | Jones | 585/414 |
| 3,850,742 | 11/1974 | Dugan et al. | 208/114 |

FOREIGN PATENT DOCUMENTS 968364 5/1975 Canada.
0268870 6/1988 European Pat. Off..

*Primary Examiner*—Glennon H. Hollrah
*Assistant Examiner*—Mark W. Russell
*Attorney, Agent, or Firm*—Dale L. Carlson

[57] ABSTRACT

A process for producing an alkylene oxide or mixture of alkylene oxides by a reaction which comprises reacting a C7 to C22 olefin or mixture thereof with an oxygen-containing gas in the presence of at least one molten nitrate salt.

15 Claims, No Drawings

ALKYLENE OXIDES PRODUCTION FROM C7 TO C22 OLEFINS USING MOLTEN NITRATE SALT CATALYST

This is a continuation-in-part application of U.S. patent application Ser. No. 929,552, filed Nov. 12, 1986, now U.S. Pat. No. 4,785,123.

BACKGROUND OF THE INVENTION

Alkylene oxides (vicinal epoxy alkanes), and particularly propylene oxide, are very valuable and widely used chemicals. They have been polymerized with a wide variety of monomers to yield polymers which are useful in coating compositions and in the manufacture of molded articles. Alkylene oxides have also been reacted with alcohols to yield monalkyl ethers which have utility as solvents in many commercial processes and which are useful as components for synthetic turboprop and turbojet lubricants.

There are many methods known in the art for the production of alkylene oxides and, most notably, propylene oxide. One of the oldest methods is the so-called "chlorohydrin process" which involves the reaction of chlorine and water to form hypochlorous acid which is then reacted with propylene to form propylene chlorohydrin. The propylene chlorohydrin is then dehydrohalogenated to yield propylene oxide. Another method to obtain propylene oxide is by the liquid phase oxidation of propylene with organic peracids. Still another method involves the liquid phase oxidation of propylene with t-butyl hydroperoxide and/or ethylbenzene hydroperoxide.

The aforementioned known methods have serious disadvantages associated therewith. For example, the "chlorohydrin process" requires the use of chlorine which is relatively expensive and corrosive in nature, requiring special handling and expensive equipment. Additionally, the chlorohydrin saponification to propylene oxide consumes alkali chemicals such as caustic soda or lime, producing a large aqueous waste stream containing chloride salts, which require costly treatment prior to discharge from the plant. The oxidation of propylene with peracids is a potentially dangerous operation and expensive equipment is needed to guard against potentially explosive hazards when working with the peracids. Another disadvantage of this method is the high cost of peracids. The t-butyl hydroperoxide and ethylbenzene hydroperoxide processes have the disadvantages of being capital-intensive, multi-step, rather complicated processes. Furthermore, these processes require co-feedstocks of isobutane or ethylbenzene, thus constraining the practical utility of the processes for propylene oxide manufacture.

Another method which has received considerable attention in the literature is the direct oxidation of hydrocarbons with an oxygen-containing gas. This method suffers from the disadvantage that it is not specific for the production of alkylene oxides but produces a variety of other compounds including acids, esters, ethers, and oxides of carbon including carbon monoxide and carbon dioxide. The reaction does, however, possess two attributes which recommend it highly for commercial utilization, i.e., inexpensiveness of starting materials and simplicity of operation. It is primarily for these reasons that much attention in recent years has been directed to improvements in methods for the production of alkylene oxides from the direct oxidation of hydrocarbons even though the producer must necessarily contend with the concurrent production of a variety of undesired products.

By way of illustration, the prior art methods which attempted to produce propylene oxide by the oxidation of propane such as that disclosed in U.S. Pat. No. 2,530,509, assigned to Linde Air Products Company, were only partially successful. The majority of the prior art methods used conventional vertical columns and differed from each other by variations in lengths and diameter of the column, temperature, pressure, etc. However, all of these methods suffered one common disadvantage—the temperature of the reactants varied throughout the length of the column.

The temperature variations are easily explained since the oxidation reactions are exothermic and the amount of heat evolved differs with each reaction which is taking place. Thus, at various increments along the tube, conditions existed which favored the direction of the oxidation to products other than propylene oxide. These prior art methods necessitated the use of elaborate and expensive cooling apparatus.

Further developments in the art constituted attempts to maximize the desired olefin oxide production while minimizing by-product formation. For example, U.S. Pat. No. 3,132,156, assigned to Union Carbide Corporation, discloses the vapor phase oxidation of saturated aliphatic hydrocarbons to olefin oxides. The method described in this '156 patent is said to provide enhanced olefin oxide production as high as 46.2 lbs per 100 lbs of $C_3$ consumed which calculates to be about 33 percent (molar) selectivity. While this level os selectivity constituted an improvement, it remains less than might be desired from a commercial standpoint. Likewise, Canadian Pat. No. 968,364, assigned to Union Carbide Corporation, discloses the indirect oxidation of olefins via the oxidation of methanol to a free radical intermediate which in turn, epoxidizes the olefin. However, the indirect oxidation method disclosed in the Canadian '364 patent has the disadvantage of requiring the use of a solvent together with subsequent solvent separation step(s). Accordingly, new methods of producing olefin oxides that combine enhanced selectivity with a simple, inexpensive process would be highly desirable.

SUMMARY OF THE INVENTION

The present invention relates to a process for producing an alkylene oxide or mixture of alkylene oxides by a reaction which comprises reacting an olefin having from 7 to 22 carbon atoms per molecule, or mixture thereof, with an oxygen-containing gas, said olefin and said oxygen-containing gas being gaseous reactants, by contacting said gaseous reactants with a bath, stream, spray or mist of at least one molten nitrate salt catalyst, said catalyst being present in an amount sufficient to absorb any heat generated during said reaction while maintaining an essentially constant reaction temperature, said reaction being conducted at a reaction temperature of between about 135° C. and about 600° C. and a reaction pressure of between about 1 and about 50 atmospheres.

DETAILED DESCRIPTION OF INVENTION

Several factors will affect the reactant conversion to alkylene oxide and the selectivity of alkylene oxide production vis-a-vis by-product production in accordance with the process of the present invention. These factors include, for example: the contact time of the molten salt with the oxygen-containing gas, the temperature of the reactor product gases, the molten salt temperature, the molten salt catalyst composition, the feed gas temperature, the feed gas composition, the feed gas pressure, and the co-catalyst employed.

The oxygen-containing gas useful as a reactant in the present invention can be any such gas. Typically, air is employed as the oxygen-containing gas based upon its ready availability. However, other oxygen-containing gases such as pure oxygen may be employed if desired, and the use of oxygen is expected to be preferred in a commercial setting.

The olefin useful in the present invention can be broadly defined as an epoxidizable, olefinically-unsaturated hydrocarbon compound having from 7 to 22 carbon atoms, preferably from 7 to 15 carbon atoms, more preferably from 7 to 12 carbon atoms, most preferably from 7 to 10 carbon atoms. This definition is intended to include terminal olefins selected from the group consisting of monofunctional and difunctional olefins having the following structural formulas respectively:

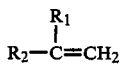

wherein $R_1$ is hydrogen or an alkyl chain, straight or branched, having 1 to 20 carbon atoms and $R_2$ is an alkyl chain, straight or branched, having 1 to 20 carbon atoms with the proviso that $R_1$ plus $R_2$ together have at least 5 carbon atoms; and

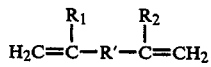

wherein $R_1$ and $R_2$ are hydrogen atoms or alkyl chains having 1 to 10 carbon atoms and $R'$ is from 2 to 10 methylene groups. The definition also includes cyclic olefins and internal olefins. The ring portions of the cyclic olefins can have up to 10 carbon atoms and one unsaturated bond and can be substituted with one or two alkyl radicals having 1 to 10 carbon atoms. The cyclic olefins are typically represented by the following structural formula:

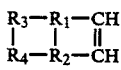

wherein $R_1$ and $R_2$ are olefin radicals having 1 to 4 carbon atoms and $R_3$ and $R_4$ represent hydrogen atoms, or one or the two alkyl radicals, straight or branched chain, having 1 to 10 carbon atoms. The internal olefins are represented by the following structural formula:

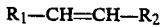

wherein $R_1$ and $R_2$ are straight chain or branched chain alkyl radicals having 1 to 10 carbon atoms with the proviso that $R_1$ plus $R_2$ together have at least 5 carbon atoms.

The olefins, and mixtures thereof, useful as reactants in accordance with the present invention generally have up to, but do not exceed, 22 carbon atoms per molecule, preferably not more than 12 carbon atoms per molecule. When a straight-chain molecule is employed, it is more preferred that such molecule not have more than ten carbon atoms. When a cyclic compound is used, it is more preferred that the cyclic compound not have more than 12 carbon atoms per molecule. A preferred reactant within this group is styrene.

Representative other olefins are heptene-1, octene-1, hexene-2, hexene-3, oxtene-2, heptene-3, pentadecene-1, octadecene-1, dodecene-2, cycloheptene, 2-methylheptene-1, and 2,4,4-trimethylpentene-1.

The olefin gas is preferably preheated to prevent condensation in the line delivering this gas to the reactor. Alternatively, both the oxygen-containing gas and the olefin gas (collectively referred to herein as "the feed gases") can be preheated to prevent condensation in any of the feed lines. However, in the absence of preheat, the molten nitrate salt will rapidly heat the feed gases up to reaction temperature. If the feed gas is preheated, it preferably is maintained at at least about 100° C. in the feed gas line(s).

The molten nitrate salt(s) catalyst is generally maintained at a temperature sufficient to keep the salt(s) in a molten condition. Preferably, the temperature is maintained between about 135° C. (275° F.) and about 600° C. (1,000° F.), more preferably between about 200° C. and about 600° C., more preferably between about 250° C. and about 550° C. during the reaction in accordance with the present invention.

The specific temperature selected is based upon the melting point of the particular molten nitrate salt chosen. For example, mixtures of molten lithium and potassium nitrate can be suitably employed at a temperature as low as about 280° F., and hence, this temperature may be employed when using lithium nitrate. In the selection of a suitable molten nitrate salt bath temperature, it is important to choose a temperature below the thermal decomposition temperature for the particular molten nitrate salt chosen. In addition, it is important to maintain a sufficient isotherm across the molten nitrate salt bath so as to avoid crust formation of the nitrate salt in the bath. Such a crust formation in the nitrate salt bath can cause localized overheating of gases trapped by the crust in the bath and an associated "runaway" oxidation reaction due to overheating of the gases in the bath. In order to maintain a bath isotherm, constant stirring of the molten nitrate salt bath is preferred. Alternatively, the molten salt can be circulated by conventional means, such as the use of internal draft tubes or external pumping loops.

The nitrate salt catalyst used may be any one of the alkali or alkaline earth nitrates such as lithium, sodium, potassium, rubidium, cesium, magnesium, calcium, strontium, or barium or mixtures thereof. In addition, the nitrate salts can be used in mixtures with other salts such as chlorides, bromides, carbonates, sulfates, and phosphates. Generally, the content of the other salt(s), when present, should be restricted to less than 60 percent by weight based upon the weight of the total melt and in most cases their contents should not exceed about 25 percent of the total melt.

The ratio of olefin to oxygen in the oxygen-containing gas in the reactor can vary over a wide range. However, in accordance with the present invention, it has now been found that enhanced selectivity of alkylene oxide product is achieved by maintaining a relatively low amount of oxygen relative to the amount of olefin fed into the reactor. For example, when reacting styrene with oxygen in a molten potassium nitrate salt column at atmospheric pressure, a ratio of between about 1 and about 20 volume percent of oxygen, e.g., about 5 volume percent oxygen to about 95 volume percent styrene is found to provide an enhanced selectivity of styrene oxide. When using air as the oxygen-containing gas, it is preferably employed in an amount of between about 5 and about 75 volume percent based upon the total amount of air plus styrene employed in the reaction. Another consideration in the selection of the amount of styrene or other olefin to use as a feed is the high partial pressure of the olefin which in high concentrations can cause thermal cracking of the olefin reactant itself. Therefore, when conducting the oxidation reaction at an elevated pressure, viz 75 psig, it is preferred to "cut" the amount of styrene in the illustrative example to 75 volume percent and utilize an inert blanket ("diluent") gas, such as nitrogen, to provide the remaining 20 volume percent of feed gas. Alternatively, the diluent gas may be comprised of mixtures of oxidation by-product gases generally readily obtainable from the styrene oxide purification operations downstream of the molten salt reactor.

In the selection of the ratio of the volume of oxygen-containing gas relative to the volume of olefin employed in the reaction mixture, the range of ratios which might pose a flammability hazard should be avoided, as is well known. For example, when utilizing an air/styrene reactant mixture at atmospheric pressure, the range of below 7 volume percent of styrene based upon total air plus styrene should be avoided.

A co-catalyst can also be utilized in accordance with the present invention. For example, when an elemental metal, or the oxide or hydroxide thereof, such as palladium, silver or molybdenum oxide, is employed as a co-catalyst in conjunction with the molten nitrate salt catalyst, it is possible to lower the reaction temperature for the particular nitrate salt selected and/or enhance the selectivity or conversion to the desired olefin oxide. By way of illustration, a palladium on alumina co-catalyst or a silver co-catalyst such as silver nitrate is expected to similarly reduce the required reaction temperatures. The use of these metal co-catalysts are preferred when the reaction is conducted at atmospheric pressure. At superatmospheric pressure, an alkali metal hydroxide co-catalyst, such as sodium hydroxide, has been found to be particularly advantageous in providing enhanced selectivity to the desired product. In addition, in a continuous process employing caustic recycle, the alkali metal hydroxide is expected to enhance the desired product distribution by removing by-product carbon dioxide by forming alkali metal carbonate.

If used, the co-catalyst is generally employed in a catalytically effective amount, generally in an amount of less than about 5 (preferably between about 0.5 and about 5, more preferably in an amount between about 0.5 and about 3) weight percent based on the total amount of co-catalyst plus molten salt catalyst.

The molten salt catalyst in which the co-catalyst (if used) is suspended or dispersed, helps to maintain the co-catalyst at a constant desired temperature or isotherm. The maintenance of the co-catalyst in such an isotherm makes it possible to reduce or avoid the problems of co-catalyst de-activation that might otherwise be encountered in a non-isothermal system due to overheating of the co-catalyst itself or due to thermal degradation of product to a tarry by-product which can coat, and thus de-activate, the catalyst.

Typically, the molten salt(s) is employed in an amount on a weight basis of between about 5 times and about 100 times (preferably between about 5 times and about 50 times) the total weight of the reactants employed.

The molten salt(s), in addition to functioning as a catalyst and as an isothermal medium for the co-catalyst, if used, also serve as a temperature regulator. More specifically, the molten nitrate salt(s) have a high heat absorption capacity, enabling them to absorb large quantities of heat during the exothermic oxidation reaction while maintaining an essentially constant reaction temperature and thereby preventing a runaway reaction. The absorbed heat of reaction from this exothermic oxidation may be employed in the process of the present invention to help maintain the molten salt in a molten state and/or to heat the gaseous reactants to reaction temperature.

In a preferred embodiment of the present invention, a mixture of potassium and sodium molten nitrate salts is employed comprising between about 20 and about 80 weight percent of sodium nitrate, preferably between about 45 and about 65 weight percent of sodium nitrate based upon the total amount of sodium nitrate and potassium nitrate in the molten salt mixture. Another preferred molten mixture is a mixture of sodium, lithium and potassium nitrate salts, preferably in a ratio of between about 10 and about 30 weight percent of lithium nitrate and between about 15 and about 75 weight percent of sodium nitrate based on the total amount of the mixture.

One method of contacting the gaseous reactants in the presence of the molten nitrate salt is by bubbling the reactants through a bath of the molten salt. If the gaseous reactants are bubbled into the bottom of the bath or column containing the molten nitrate salt, the contact time of the reactants with the molten salt catalyst is equal to the "rise time" of the reactants through the bath or column. Thus, the contact time can be increased by increasing the length of the molten nitrate salt bath or column. An alternate method of contacting the gaseous reactants in the presence of the molten salt would be to pass the gaseous reactants through a reactor counter-currently to a spray or mist of the molten salt. This latter method is preferred since it provides for enhanced surface area contact of the reactants with the molten salt. Still another method of contacting the gaseous reactants with molten salt would be to inject the reactants into a circulating stream of molten salt, wherein the kinetic energy of both streams is utilized to provide intimate mixing through the application of nozzles, mixers, and other conventional equipment. This latter method is expected to be preferred in a commercial setting. These methods are only illustrative of types of reaction systems which may be employed in the practice of this disclosure. Other conventional methods of gas-liquid contact in reaction systems may also be employed.

The olefin feed gas(es) can be passed into the molten nitrate salt-containing reactor using a separate stream (e.g. feed tube) from the stream delivering the oxygen-containing gas to the reactor. Alternatively, the reactant gases can be fed into the reactor together in a single stream. In a preferred embodiment of the present invention, two co-axially-mounted feed gas tubes are employed. The co-axial mounting of the feed gas tubes has been found to reduce or minimize the back-up of molten salt into an unpressurized feed tube if pressure is temporarily lost in either (but not both) feed tube. Mixing of the gaseous reactants prior to, or at the point of, the gas(es) inlet into the reactor is desired in order to facilitate the oxidation reaction. Mixing is suitably accomplished using an impingement mixer or sparger tube.

If a molten salt bath is used, the feed gas is preferably bubbled into the molten nitrate salt-containing reactor using a sparger. If used, the sparger is preferably positioned in the molten nitrate salt to a sparger exit port depth of between about 2 and about 1000 centimeters, preferably between about 10 and about 200 centimeters, depending upon the size of the reactor utilized and the overall depth of the molten salt in the reactor. Alternatively, the gas can be fed directly into the bottom of the reactor by a feed tube. The feed gas tubes are preferably co-axially mounted so that in the event of a loss of pressure in either gas tube, the gas in the other tube will maintain sufficient pressure to keep the molten salt from backing up into the unpressurized feed gas tube.

This process can be run in a batchwise or continuous operation, the latter being preferred. The order of introduction of the reactants is determined by the operator based on what is most safe and practical under prevalent conditions. Generally, the desirability of avoiding flammable gas mixtures throughout the reaction and subsequent product separation systems will dictate the desired procedures.

The process can be carried out by feeding a mixture of olefin, inert gas, and oxygen into a reaction vessel containing molten nitrate salt. The reaction vessel can be glass, glass-lined metal, or made of titanium. For example, a glass-lined stainless steel autoclave can be used, although, even better from a commercial point of view, is an unlined type 316 stainless steel autoclave (as defined by the American Iron and Steel Institute). A tubular reactor made of similar materials can also be used together with multi-point injection to maintain a particular ratio of reactants. Other specialized materials may be economically preferred to minimize corrosion and contamination of the molten salt and products, or to extend the useful life of the reaction system.

Some form of agitation of the molten salt(s)/feed gas mixture is preferred to avoid a static system and insure the homogeneity of the molten salt, agitation help prevent crust formation of the salt(s) at the head gas/salt interface in the reactor. This can be accomplished by using a mechanically stirred autoclave, a multi-point injection system, or a continuous process, e.g., with a loop reactor wherein the reactants are force circulated through the system. Sparging can also be used. In the subject process, it is found that increased rates of reaction are obtained by good gas-liquid contact provided by agitation of the molten salt/gas mixture.

The process of the present invention is suitably carried out at atmospheric, subatmospheric or superatmospheric pressure. Typically, the process is effected at superatmospheric pressures of up to about 100 atmospheres, preferably between about 1 atmosphere and about 50 atmospheres, more preferably between about 1 atmosphere and about 35 atmospheres. The most preferred pressure range is between about 1 and about 25 atmospheres.

It is to be understood that by-products are also produced during the reaction. For example, some oxidative cracking of the styrene feed is also effected, particularly at higher temperatures within the hereinabove noted temperature range, and therefore, the reaction conditions are generally controlled to minimize such production. The separation of the resulting by-products in order to recover the desired product may be effected by a wide variety of well-known procedures such as: absorption in water followed by fractional distillation, absorption, and condensation.

The following examples are intended to illustrate, but in not way limit the scope of, the present invention.

PROPOSED EXAMPLE 1

Styrene Oxidation to Styrene Oxide

A 6 liter cylindrical stainless steel autoclave reactor approximately 68 cm deep and 9 cm in diameter is filled with 3600 g of sodium nitrate and 2400 g of potassium nitrate. The salt mixture is melted and brought up to 350° C. by way of externally wrapped electrical resistance heating coils. Styrene at a feed rate of 0.5 ml/min is injected into a feed tube extending into the salt to a depth of about ½ inch from the bottom of the reactor. Oxygen, at a feed rate of 200 cc/min, and nitrogen at a feed rate of 1000 cc/min, are fed through the same tube in order to sweep the styrene into the reactor. The end of the feed tube is equipped with a sparging element in order to get better dispersion inside the reactor. The reactor pressure is held at 150 psig for 30 minutes with continuous gas flow into and out of the reactor. After this time period, the reactant feeds are stopped, ending the reaction. A dry ice-isopropanol trap in-line after the reactor is used to condense reaction products and unreacted styrene. The gas exiting the trap is collected in a sample cylinder. Gas chromatographic and GC/MS analysis of the condensate and reaction off gases shows that the major reaction products are styrene oxide, benzaldehyde, phenylacetaldehyde, carbon monoxide, and carbon dioxide.

PROPOSED EXAMPLE 2

1-Tert-Butylcyclohexene Oxidation to
1-Tert-Butylcyclohexene Oxide

A reaction is carried out in the same way as in PROPOSED EXAMPLE 1, except that 1-tert-butylcyclohexene is used instead of styrene. After a reaction run time of 30 minutes, the reactant flows are stopped. Gas chromatographic and GC/MS analysis of the reaction condensate and off gases shows that the major products are 1-tert-butylcyclohexene oxide, 1-tert-butyl-2-cyclohexenone, and 6-keto-7,7-dimethyloctanal.

PROPOSED EXAMPLE 3

2-Methyl-1-Undecene Oxidation to
2-Methyl-1,2-Epoxyundecane

A reaction is carried out in the same way as in EXAMPLE 1, except that 2-methyl-1-undecene is used instead of styrene. The run is allowed to proceed for 30 minutes and then reactant flows are stopped. Gas chromatographic and GC/MS analysis of the reaction condensate and off gases shows that the major products are 2-methyl-1,2-epoxyundecane, methylnonyl ketone, carbon monoxide, and carbon dioxide.

What is claimed is:

1. A process for producing an alkylene oxide or mixture of alkylene oxides by a reaction which comprises reacting an olefin having from 7 to 22 carbon atoms per molecule, or mixture thereof, with an oxygen-containing gas, said olefin and said oxygen-containing gas being gaseous reactants, by contacting said gaseous reactants with a bath, stream, spray or mist of at least one molten nitrate salt catalyst, and optionally a co-catalyst, and said catalyst being present in an amount sufficient to absorb any heat generated during said reaction while maintaining an essentially constant reaction temperature, said reaction being conducted at a reaction temperature of between about 135° C. and about 600° C. and a reaction pressure of between about 1 and about 50 atmospheres.

2. The process of claim 1 wherein said co-catalyst is an alkali metal hydroxide.

3. The process of claim 2 wherein said alkali metal hydroxide is selected from the group consisting of sodium hydroxide, potassium hydroxide, and combinations thereof.

4. The process of claim 1 wherein said co-catalyst is palladium, silver, molybdenum oxide, or a salt thereof.

5. The process of claim 1 wherein said molten nitrate salt is selected from the group consisting of sodium, potassium, lithium, cesium, magnesium, and calcium molten nitrate salts and mixtures thereof.

6. A method for producing an alkylene oxide from an olefin having from 7 to 22 carbon atoms per molecule or mixture thereof, which comprises bubbling gaseous reactants consisting of an oxygen-containing gas and said olefin, or mixture thereof, through a bath of at least one molten nitrate salt catalyst and optionally a co-catalyst, and, said catalyst being present in an amount sufficient to absorb any heat generated during said reaction while maintaining an essentially constant reaction temperature, said reaction being conducted at a reaction temperature of between about 135° C. and about 600° C. and a reaction pressure of between about 1 and about 50 atmospheres.

7. The method of claim 6 wherein said oxygen-containing gas is fed into said bath by means of a first tube and wherein said olefin, or mixture thereof, is fed into said bath by means of a second tube.

8. The method of claim 7 wherein said first tube and said second tube are co-axially mounted with respect to each other.

9. The method of claim 6 wherein said olefin, or mixture thereof, has between 7 and 15 carbon atoms per molecule on average.

10. The process of claim 6 wherein said co-catalyst is an alkali metal hydroxide.

11. The process of claim 10 wherein said co-catalyst is selected from the group consisting of sodium hydroxide, potassium hydroxide, and combinations thereof.

12. A process for producing an alkylene oxide or mixture of alkylene oxides by a reaction which comprises reacting an olefin having from 7 to 12 carbon atoms per molecule, or mixture thereof, with an oxygen-containing gas, said olefin and said oxygen-containing gas being gaseous reactants, by contacting said gaseous reactants with a bath, stream, spray or mist of at least one molten nitrate salt catalyst, and optionally a co-catalyst, and said catalyst being present in an amount sufficient to absorb any heat generated during said reaction while maintaining an essentially constant reaction temperature, said reaction being conducted at a reaction temperature of between about 135° C. and about 600° C. and a reaction pressure of between about 1 and about 50 atmospheres.

13. The process of claim 12 wherein said olefin has from 7 to 10 carbon atoms per molecule.

14. The process of claim 12 wherein said alkali metal hydroxide is selected from the group consisting of sodium hydroxide, potassium hydroxide, and combinations thereof.

15. The process of claim 12 wherein said co-catalyst is palladium, silver, molybdenum oxide, or a salt thereof.

* * * * *